(12) United States Patent
Wang et al.

(10) Patent No.: US 9,790,323 B2
(45) Date of Patent: Oct. 17, 2017

(54) POLYMER CONDUCTOR FOR LITHIUM-ION BATTERIES

(71) Applicant: The Penn State Research Foundation, University Park, PA (US)

(72) Inventors: Qing Wang, Collegeville, PA (US); Kui Xu, Rolla, MO (US)

(73) Assignee: The Penn State Research Foundation, University Park, PA (US)

( * ) Notice: Subject to any disclaimer, the term of this patent is extended or adjusted under 35 U.S.C. 154(b) by 5 days.

(21) Appl. No.: 14/419,059

(22) PCT Filed: Jul. 26, 2013

(86) PCT No.: PCT/US2013/052259
§ 371 (c)(1),
(2) Date: Feb. 2, 2015

(87) PCT Pub. No.: WO2014/022224
PCT Pub. Date: Feb. 6, 2014

(65) Prior Publication Data
US 2015/0218313 A1 Aug. 6, 2015

Related U.S. Application Data

(60) Provisional application No. 61/678,834, filed on Aug. 2, 2012.

(51) Int. Cl.
*C08G 79/00* (2006.01)
*C08G 65/38* (2006.01)
(Continued)

(52) U.S. Cl.
CPC ............ *C08G 65/38* (2013.01); *C07C 309/07* (2013.01); *C08G 65/007* (2013.01);
(Continued)

(58) Field of Classification Search
CPC .... C08G 65/38; C07C 309/07; H01M 10/052; H01M 10/0565
See application file for complete search history.

(56) References Cited

U.S. PATENT DOCUMENTS

2012/0004417 A1    1/2012   Dimagno

FOREIGN PATENT DOCUMENTS

| JP | 2012018909 | 1/2012 | |
| WO | WO 9967304 | * 12/1999 | ........... C07C 309/11 |
| WO | 0063998 | 10/2000 | |
| WO | 2012059222 | 5/2012 | |

OTHER PUBLICATIONS

International Search Report and the Written Opinion of the International Searching Authority, mailed Dec. 2, 2013.
(Continued)

*Primary Examiner* — Shane Fang
(74) *Attorney, Agent, or Firm* — Buchanan Ingersoll & Rooney PC

(57) ABSTRACT

We report a new class of single-ion electrolyte including pendant lithium perfluoroethyl sulfonates. Embodiments may be based on, for example, aromatic poly(arylene ether)s, polyphenylenes, or polyarylene sulfides. The microporous polymer film saturated with organic carbonates exhibits a nearly unity $t_{Li+}$, state-of-the-art conductivities (e.g. $>10^{-3}$ S cm$^{-1}$ at room temperature) over a wide range of temperatures, high electrochemical stability, and outstanding mechanical properties, which enables the membrane to function as both ion conducting medium and separator in the batteries.

20 Claims, 8 Drawing Sheets

(51) Int. Cl.
*H01M 10/0525* (2010.01)
*H01M 10/0565* (2010.01)
*C08J 5/18* (2006.01)
*C08J 5/22* (2006.01)
*C07C 309/07* (2006.01)
*H01M 10/052* (2010.01)
*C08G 65/00* (2006.01)
*C08G 65/40* (2006.01)
*C08L 71/12* (2006.01)

(52) U.S. Cl.
CPC ............ *C08G 65/4006* (2013.01); *C08J 5/18* (2013.01); *C08J 5/2262* (2013.01); *C08L 71/12* (2013.01); *H01M 10/052* (2013.01); *H01M 10/0525* (2013.01); *H01M 10/0565* (2013.01); *H01M 2300/0085* (2013.01); *Y02T 10/7011* (2013.01)

(56) References Cited

OTHER PUBLICATIONS

Xu, K. et al., Highly Conductive Aromatic Ionomers With Perfluorosulfonic Acid Side Chains for Elevated Temperature Fuel Cells, Macromolecules, 2011, vol. 44, No. 12, pp. 4605-4609.

Ayothi, R. et al., Arylonium Photoacid Generators Containing Enviromentally Compatible Aryloxyperfluoroalkanesulfonate Groups, Chemistry of Materials, 2007, vol. 19, 1434-1444.

\* cited by examiner

POLYMER CONDUCTOR FOR LITHIUM-ION BATTERIES

CROSS-REFERENCE TO RELATED APPLICATIONS

This application is the national phase under 35 U.S.C. §371 of PCT International Application No. PCT/US2013/052259, filed on Jul. 26, 2013, which claims priority to U.S. Provisional Patent App. No. 61/678,834, which was filed on Aug. 2, 2012, and is incorporated by reference herein.

BACKGROUND OF THE INVENTION

Field of the Invention

Embodiments of the invention relate to polymers that are conductors and to lithium-ion batteries made from those conductors. In typical embodiments the polymers are used as single-ion conductors.

Background of the Related Art

For some time, lithium-ion batteries have been the technology of choice as rechargeable energy storage devices for portable electronics and electric vehicles. Electrolytes that conduct electricity by ions between electrodes constitute an integral part in lithium-ion batteries. Single-ion conducting electrolytes in which the anionic species is anchored to a polymer and becomes immobile present a unique alternative to traditional binary salt conductors.

Theoretically, single-ion electrolytes with a lithium-ion transference number ($t_{Li+}$) of unity can eliminate the salt concentration gradient and polarization loss in the cell that develops in a binary salt system. This results in substantial improvements in materials utilization for high power and energy densities. Traditionally the best single-ion electrolytes have ambient temperature Li$^+$ conductivities in the range of $10^{-7}$~$10^{-5}$ S cm$^{-1}$, which are at least two orders of magnitude smaller for practical applications.

Nearly all of liquid and polymer electrolytes that currently prevail in both prototype and commercial lithium-ion batteries have been binary salt conductors where both lithium ions and their counter-anions migrate between electrodes during charging and discharging process. The conductivity of binary salt conductors is actually dominated by the motion of anions, as anions of salt have very high mobility and move 5-10× faster than Li$^+$ regardless of the choice of anion. For example, polymer electrolytes composed of the Li salts (e.g. LiXF$_6$, X=P, As, Sb) dissolved in coordination polymers, such as poly(ethylene oxide) (PEO), typically have a value of $t_{Li+}$ between 0.2 and 0.3, i.e., only 20-30% of the measured conductivity is associated with Li$^+$ mobility.

There is, however, no electrode reaction for the anions. As a result, the buildup of the anions at the electrode/electrolyte interface causes concentration polarization, leading to loss of power drawn from the battery. Hence, the free movement of anions needs to be limited or totally eliminated, which has been realized by covalent attachment of the anions to the polymer backbones to form single ion conductors (i.e. ionomers).

Due to the size and relatively immobile nature of the polymer chains, only cations are able to migrate over long distances in the solid state on reasonable time scales, and a unity $t_{Li+}$ can be achieved in single-ion conductors. The advantages of the employment of single-ion conductors in batteries have been long recognized, including a spatially uniform anion distribution that enables the passage of larger currents through the cell, and lower joule heat per unit of current that lessens the chance of thermal runaway, and the absence of electrochemical interactions of anions with electrodes for improved stability.

Several classes of single-ion conductors have been reported in the past, however with modest success, as this approach significantly depresses the overall electrolyte conductivity. It has been widely accepted that ion conduction in polymer electrolytes is strongly correlated with the local segmental motion and thus with the glass transition phenomena of the polymers.

Consequently, the known single-ion conductors are mainly based on low-glass transition temperature ($T_g$) polymers such as PEO and polysiloxane. These approaches so far only resulted in limited improvement in room-temperature ionic conductivity. Moreover, the utilization of the low-$T_g$ polymers may scarify the mechanical integrity and thermal stability of the membranes, which is an additional hurdle for the single-ion conductors as they are also often expected to play the role of separators between the electrodes.

BRIEF SUMMARY OF THE INVENTION

We report a new class of single-ion electrolyte including pendant lithium perfluoroethyl sulfonates. Embodiments may be based on, for example, aromatic poly(arylene ether)s, polyphenylenes, or polyarylene sulfides. The microporous polymer film saturated with organic carbonates exhibits a nearly unity $t_{Li+}$, state-of-the-art conductivities (e.g. >$10^{-3}$ S cm$^{-1}$ at room temperature) over a wide range of temperatures, high electrochemical stability, and outstanding mechanical properties, which enables the membrane to function as both ion conducting medium and separator in the batteries.

Excellent cyclability with almost identical charge and discharge capacities have been demonstrated in the cells assembled from the single-ion conductors. This work will open a new avenue to accelerate the development of high-performance electrolytes for lithium-ion batteries. Methods of making these polymers and polyer films are reported herein. Batteries formed from these materials are also disclosed.

Various embodiments of the invention are shown and described herein. For example, one embodiment provides a polymer of Formula (II):

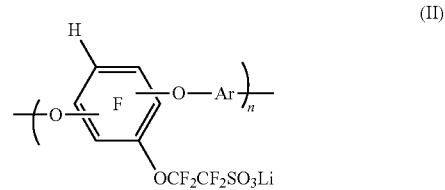

where n and z are between 10-1000, and wherein Ar is one or more of the following, with * showing points of connection or termination:

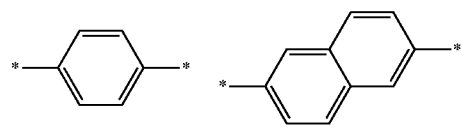

-continued

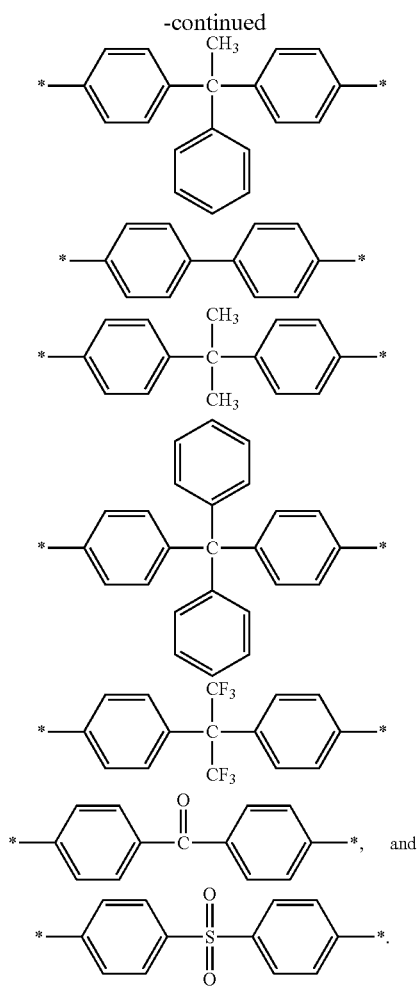

In a preferred embodiment the compound is fluorinated poly(arylene ether) lithium perfluoroethyl sulfonate. In another embodiment the polymer of formula (II) is provided and Ar is

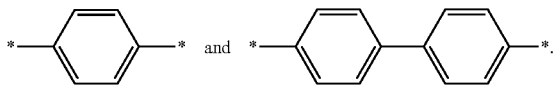

A further embodiment provides a compound of Formula (I),

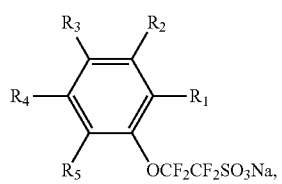

wherein $R_1$, $R_2$, and $R_3$ are independently selected from the group consisting of H, F, Cl, Br, I, CN, $C_nH_{2n+1}$, $OC_nH_{2n+1}$, and $C(=O)OC_nH_{2n+1}$, wherein $1 \le n \le 10$.

The compound of Formula (I) allows many variations and substitutions. In some particular instances R1, R2, R3, R4, and R5 are a set selected as follows: $R_1$ is F, $R_2$ is F, $R_3$ is H, $R_4$ is F, and $R_5$ is F; $R_1$ is F, $R_2$ is F, $R_3$ is H, $R_4$ is F, and $R_5$ is H; $R_1$ is F, $R_2$ is H, $R_3$ is F, $R_4$ is F, and $R_5$ is H; $R_1$ is H, $R_2$ is F, $R_3$ is F, $R_4$ is F, and $R_5$ is H; $R_1$ is H, $R_2$ is F, $R_3$ is CN, $R_4$ is F, and $R_5$ is H; $R_1$ is Cl, $R_2$ is H, $R_3$ is H, $R_4$ is Cl, and $R_5$ is H; $R_1$ is Cl, $R_2$ is H, $R_3$ is H, $R_4$ is H, and $R_5$ is Cl; $R_1$ is H, $R_2$ is Cl, $R_3$ is H, $R_4$ is Cl, and $R_5$ is H; $R_1$ is Br, $R_2$ is H, $R_3$ is H, $R_4$ is Br, and $R_5$ is H; $R_1$ is Br, $R_2$ is H, $R_3$ is H, $R_4$ is H, and $R_5$ is Br; $R_1$ is H, $R_2$ is Br, $R_3$ is H, $R_4$ is Br, and $R_5$ is H; $R_1$ is I, $R_2$ is H, $R_3$ is H, $R_4$ is I, and $R_5$ is H; $R_1$ is I, $R_2$ is H, $R_3$ is H, $R_4$ is H, and $R_5$ is I; and $R_1$ is H, $R_2$ is I, $R_3$ is H, $R_4$ is I, and $R_5$ is H.

In a further embodiment the compound is sodium 2-(2', 3',5',6'-tetrafluorophenoxyl) perfluoroethane sulfonate and sodium 2-(2',5'-dichorophenoxy) perfluoroethane sulfonate.

Embodiments also provide methods of synthesis. For example, we provide a method for synthesis of the compound of Formula (I), including the steps of:

(a) subjecting a compound of the following formula:

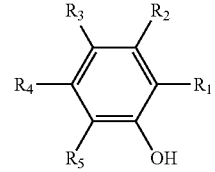

to 1,2-dibromoethane, where R1, R2, R3, R4, and R5 are independently selected from the group consisting of H, F, Cl, Br, I, and CN, thereby preparing a compound of the following formula:

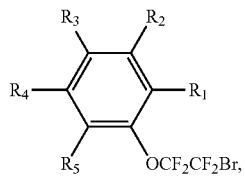

and subjecting that compound to sodium hydrosulfite/sodium bicarbonate and hydrogen peroxide.

In some embodiments the various substituents contemplated by the compound of the prior paragraph are present in particular configurations. For example, in some embodiments R1, R2, R3, R4, and R5 are selected from: $R_1$ is F, $R_2$ is F, $R_3$ is H, $R_4$ is F, and $R_5$ is F; $R_1$ is F, $R_2$ is F, $R_3$ is H, $R_4$ is F, and $R_5$ is H; $R_1$ is F, $R_2$ is H, $R_3$ is F, $R_4$ is F, and $R_5$ is H; $R_1$ is H, $R_2$ is F, $R_3$ is F, $R_4$ is F, and $R_5$ is H; $R_1$ is H, $R_2$ is F, $R_3$ is CN, $R_4$ is F, and $R_5$ is H; $R_1$ is Cl, $R_2$ is H, $R_3$ is H, $R_t$ is Cl, and $R_5$ is H; $R_1$ is Cl, $R_2$ is H, $R_3$ is H, $R_4$ is H, and $R_5$ is Cl; $R_1$ is H, $R_2$ is Cl, $R_3$ is H, $R_4$ is Cl, and $R_5$ is H; $R_1$ is Br, $R_2$ is H, $R_3$ is H, $R_4$ is Br, and $R_5$ is H; $R_1$ is Br, $R_2$ is H, $R_3$ is H, $R_4$ is H, and $R_5$ is Br; $R_1$ is H, $R_2$ is Br, $R_3$ is H, $R_4$ is Br, and $R_5$ is H; $R_1$ is I, $R_2$ is H, $R_3$ is H, $R_1$ is I, and $R_5$ is H; $R_1$ is I, $R_2$ is H, $R_3$ is H, $R_4$ is H, and $R_5$ is I; and $R_1$ is H, $R_2$ is I, $R_3$ is H, $R_4$ is I, and $R_5$ is H.

Further embodiments of the invention provide a polymer having Formula I(a):

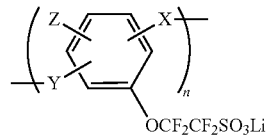

wherein n is between 10 and 1000;
wherein Z is halogen, cyano, or hydrogen; and X and Y may be the same or different and are independently selected from:

a bond, or one or more of phenyl, sulfur, oxygen, sulfonyl, phenylthio, phenylthiobenzenethiolyl, phenylsulfonyl, and —O—Ar, wherein Ar is selected from the group consisting of:

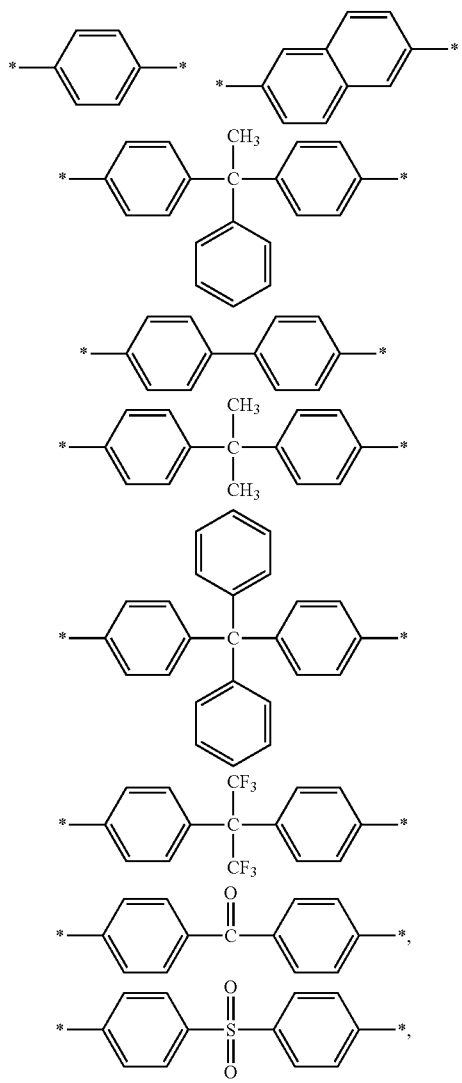

and combinations thereof.

Further embodiments provide more specific subgenera within the preceding genus. These may, for examples, polymers having one of the following formulas:

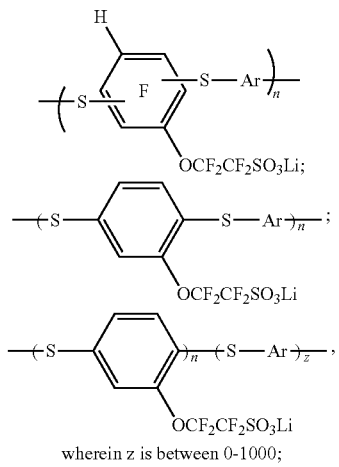

wherein z is between 0-1000;

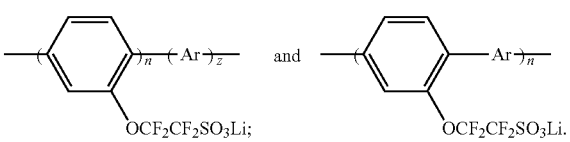

Embodiments may also provide a method for preparing a lithium single-ion conductor. The method may include the steps of preparing a plurality of aromatic monomers, wherein each of said aromatic monomers has at least one lithium sulfonate substituent; and condensing said plurality of aromatic monomers to form a polymer comprising repeating lithium sulfonate substituents, wherein said polymer is a lithium single-ion conductor.

Polymers as reported herein may be used in porous polymer films. These films may be used as single-ion conductors in batteries, for example, in lithium-ion battery cells, or in other applications. In some embodiment they are combined with an ionic liquid to form an additional conductor.

BRIEF DESCRIPTION OF THE FIGURES

FIG. 4(bottom) shows impedance response of a PAE-LiPFS/DEC+EC+PC film. The inset shows time dependence of the ionic conductivity of the electrolyte film at 25° C. Data obtained by impedance spectroscopy measurements.

FIG. 5(bottom) shows the first galvanostatic (current density=17 mA g$^{-1}$) charge-discharge voltage profile of the LiFePO$_4$/electrolyte film/Li cell at room temperature. The inset shows the coulombic efficiency and cyclability of the cell.

DETAILED DESCRIPTION OF THE INVENTION

Figure 1:
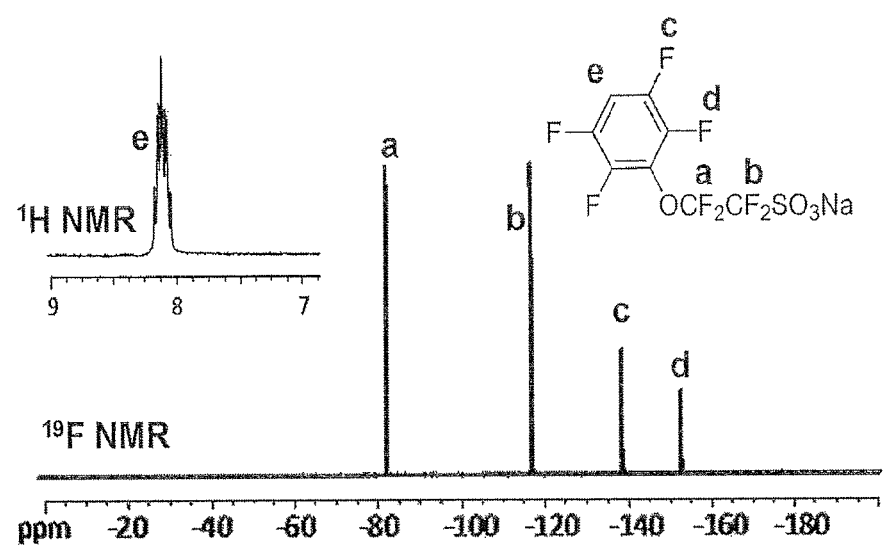
FIG. 1 shows $^1$H NMR (the inset) and $^{19}$F NMR spectra of the monomer TFP as prepared in Example 1.

Embodiments of the invention provide various polymers, polymer films, and batteries including those polymer films. Typical embodiments include pendent perfluorosulfonated lithium substituents. Methods of making those compositions are also contemplated herein. Although not meant to be limiting of any embodiments disclosed herein, typical embodiments entail preparing aromatic monomers that have lithium sulfonate groups first, then using condensation polymerization to obtain polymers.

Embodiments present an example of single-ion electrolytes possessing many remarkable features for lithium-ion batteries, including high ionic conductivities that reach practically useful values for the first time, and great mechanical, thermal and electrochemical stability in addition to almost unity $Li^+$ transfer number. The demonstrated excellent cell performance on the prepared single-ion conductors further denotes it potential for practical applications. The absence of $PF_6^-$, the preferred anion of the currently used organic liquid electrolytes, in the single-ion conductors is expected to improve the battery lifetime and enable use of new electrode materials not previously considered acceptable due to the metal dissolution issue (e.g. Mn dissolution from $LiMn_2O_4$ positive electrode). Combined with versatile structures of aromatic polymers and great flexibility in molecular design and synthesis, this approach would broaden greatly the scope of electrolytes for advanced electrochemical devices.

I. Monomers

Polymers of the invention are typically prepared by polymerization of monomers of Formula (I):

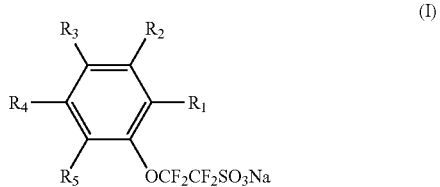

(I)

wherein $R_1$, $R_2$, $R_3$, $R_4$ and $R_5$ are independently selected from the group consisting of H, F, Cl, Br, I, CN, $C_nH_{2n+1}$, $OC_nH_{2n+1}$, and $C(=O)OC_nH_{2n+1}$ (n≥1). In preferred embodiments n has a range of 1 to 10. In other embodiments n is between 1 and 6.

These monomers may be prepared, for example, by the reaction scheme set forth below:

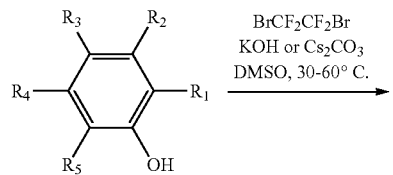

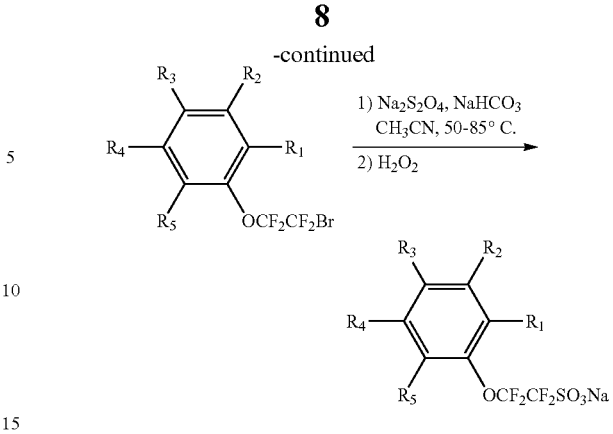

In that reaction scheme, $R_1$, $R_2$, $R_3$, $R_4$, and $R_5$ are independently selected from the group consisting of H, F, Cl, Br, I, CN, $C_nH_{2n+1}$, $OC_nH_{2n+1}$, and $C(=O)OC_nH_{2n+1}$ (n≥1). In preferred embodiments the following selections are made:
$R_1$ is F, $R_2$ is F, $R_3$ is H, $R_4$ is F, and $R_5$ is F; $R_1$ is F, $R_2$ is F, $R_3$ is H, $R_4$ is F, and $R_5$ is H; $R_1$ is F, $R_2$ is H, $R_3$ is F, $R_4$ is F, and $R_5$ is H; $R_1$ is H, $R_2$ is F, $R_3$ is F, $R_4$ is F, and $R_5$ is H; $R_1$ is H, $R_2$ is F, $R_3$ is CN, $R_4$ is F, and $R_5$ is H; $R_1$ is Cl, $R_2$ is H, $R_3$ is H, $R_4$ is Cl, and $R_5$ is H; $R_1$ is Cl, $R_2$ is H, $R_3$ is H, $R_4$ is H, and $R_5$ is Cl; $R_1$ is H, $R_2$ is Cl, $R_3$ is H, $R_4$ is Cl, and $R_5$ is H; $R_1$ is Br, $R_2$ is H, $R_3$ is H, $R_4$ is Br, and $R_5$ is H; $R_1$ is Br, $R_2$ is H, $R_3$ is H, $R_4$ is H, and $R_5$ is Br; $R_1$ is H, $R_2$ is Br, $R_3$ is H, $R_4$ is Br, and $R_5$ is H; $R_1$ is I, $R_2$ is H, $R_3$ is H, $R_4$ is I, and $R_5$ is H; $R_1$ is I, $R_2$ is H, $R_3$ is H, $R_4$ is H, and $R_5$ is I; $R_1$ is H, $R_2$ is I, $R_3$ is H, $R_4$ is I, and $R_5$ is H.

EXAMPLE 1

This example reports synthesis of sodium 2-(2',3',5',6'-tetrafluorophenoxy) perfluoro-ethane sulfonate ("TFP"). This chemical structure is shown in Structure (I) with the selections of R1, R2, R4 and R5 as F, and R3 as H).

In a 500 mL three-neck flask fitted with a refluxing condenser and a dropping funnel were added 2,3,5,6-tetrafluorophenol (20 g), dry cesium carbonate (60 g), 1,2-dibromotetrafluoroethane (47 g) and anhydrous DMSO (75 mL) under argon. The reaction mixture was stirred at 35° C. for 6 hours and 50° C. for 10 hours. After cooling to room temperature, the mixture was poured into a beaker with dichloromethane (150 mL) and water (150 mL) and underwent vigorously stirring for 30 minutes. The organic phase (dichloromethane) was separated and the aqueous phase was extracted with dichloromethane (2×50 mL). The combined dichloromethane solution was then washed with water (2×50 mL), brine (50 mL) and dried over $Na_2SO_4$. After removal of the solvent under reduced pressure, the residue was dried at 60° C. in vacuum oven for overnight to give a light yellow liquid, 2'-bromotetrafluroroethoxy 2,3,5,6-tetrafluoro benzene (34.5 g, yield: 83%, $^1H$ NMR ($d^6$-DMSO, ppm): δ 8.1 (m, 1H, Ar—H). 19F NMR ($d^6$-DMSO, ppm): δ −71.4 (s, 2F, —$CF_2$Br), −86.8 (s, 2F, —$OCF_2$—), −133.5 (s, 2F, Ar—F), −151.9 (s, 2F, Ar—F)). In a flask fitted with a refluxing condenser were added 2'-bromotetrafluroroethoxy 2,3,5,6-tetrafluorobenzene (20.7 g), $NaHCO_3$ (11.7 g), $Na_2S_2O_4$ (24.4 g) and a mixture of water (110 mL) and acetontrile (55 mL).

The reaction mixture was stirred at 70° C. for 12 hours under the protection of argon. After cooling down to room temperature, ethyl acetate (60 mL) was added and the organic phase was separated. The aqueous phase was extracted by ethyl acetate (2×50 mL). The combined ethyl acetate solution was then washed by brine (2×50 mL), dried over Na$_2$SO$_4$ and then dried under reduced pressure. The white waxy solid obtained was re-dissolved in ethyl acetate (10 mL), precipitated in hexane, and dried under vacuum at 60° C. for 12 h to give sodium 2-(2',3',5',6'-tetrafluorophenoxy) perfluoro-ethane sulfinate (18.7 g).

In a flask, the prepared sodium 2-(2',3',5',6'-tetrafluorophenoxy) perfluoro-ethane sulfinate was dissolved in a mixture of hydrogen peroxide aqueous solution (30%, 12 mL) and water (30 mL). After being stirred at room temperature for 10 hours, the solution was dried under reduced pressure. The solid residue was dissolved in ethyl acetate and precipitated from hexane. The product obtained, sodium 2-(2', 3',5',6'-tetrafluorophenoxy) perfluoro-ethane sulfonate, was then dried under vacuum at 100° C. for 24 hours (15.8 g, 71%). $^1$H NMR (d$^6$-DMSO, ppm): δ 8.1 (m, 1H, Ar—H). $^{19}$F NMR (d$^6$-DMSO, ppm): δ −82.7 (s, 2F, —OCF$_2$—), −117.8 (s, 2F, —CF$_2$—SO$_3$Na), −138.9 (s, 2F, Ar—F), −152.7 (s, 2F, Ar—F). Elemental analysis, calculated: C, 26.1; H, 0.3; F, 41.3; O, 17.4; S, 8.7. Found: C, 26.0; H, 0.3; F, 41.2; O, 17.5; S, 8.7.

EXAMPLE 2

Example 2 reports synthesis of sodium 2-(2',5'-dichlorophenoxy) perfluoro-ethane sulfonate. The chemical structure of this is shown in Structure (I) when, R1 and R4 are Cl, and R2, R3, and R5 are H).

In a 500 mL three-neck flask fitted with a refluxing condenser and a dropping funnel were added 2,5-dichlorophenol (11 g), dry cesium carbonate (60 g), 1,2-dibromotetrafluoroethane (47 g) and anhydrous DMSO (75 mL) under argon. The reaction mixture was stirred at 35° C. for 6 hours and 50° C. for 10 hours. After cooling to room temperature, the mixture was poured into a beaker with dichloromethane (150 mL) and water (150 mL) and underwent vigorously stirring for 30 minutes. The organic phase (dichloromethane) was separated and the aqueous phase was extracted with dichloromethane (2×50 mL). The combined dichloromethane solution was then washed with water (2×50 mL), brine (50 mL) and dried over Na$_2$SO$_4$. After removal of the solvent under reduced pressure, the residue was dried at 60° C. in vacuum oven for overnight to give a light yellow liquid, 2'-bromotetrafluroroethoxy 2,5,-dichlorobenzene (28.2 g, yield: 87%). In a flask fitted with a refluxing condenser were added 2'-bromotetrafluroroethoxy 2,5,-dichlorobenzene (16.2 g), NaHCO$_3$ (11.7 g), Na$_2$S$_2$O$_4$ (24.4 g) and a mixture of water (110 mL) and acetontrile (55 mL).

The reaction mixture was stirred at 70° C. for 12 hours under the protection of argon. After cooling down to room temperature, ethyl acetate (60 mL) was added and the organic phase was separated. The aqueous phase was extracted by ethyl acetate (2×50 mL). The combined ethyl acetate solution was then washed by brine (2×50 mL), dried over Na$_2$SO$_4$ and then dried under reduced pressure. The white waxy solid obtained was re-dissolved in ethyl acetate (10 mL), precipitated in hexane, and dried under vacuum at 60° C. for 12 h to give sodium 2-(2',5'-dichlorophenoxy) perfluoro-ethane sulfinate (15.9 g). In a flask, the prepared sodium 2-(2',5'-dichlorophenoxy) perfluoro-ethane sulfinate was dissolved in a mixture of hydrogen peroxide aqueous solution (30%, 12 mL) and water (30 mL). After being stirred at room temperature for 10 hours, the solution was dried under reduced pressure. The solid residue was dissolved in ethyl acetate and precipitated from hexane. The product obtained, sodium 2-(2', 5',dichlorophenoxy) perfluoro-ethane sulfonate, was then dried under vacuum at 100° C. for 24 hours (13.4 g, 76%). $^1$H NMR and $^{19}$F NMR (FIG. 1), d$^6$-DMSO, ppm. As was typical for experiments described in this disclosure, for $^1$H NMR, we dissolved 5 mg of sample in 0.6 ml d$^6$-DMSO, and did the NMR test at room temperature with 64 scans. For $^{19}$F NMR, A higher concentration of 25 mg/0.6 ml d$^6$-DMSO was used, and the test was also done at room temperature with 160 scans.

II. General Polymers

Embodiments of the invention may provide polymers having the general formula shown in Formula I(a):

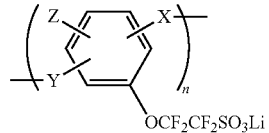

wherein n is between 10 and 1000;

Z is halogen, cyano, or hydrogen; and X and Y may be the same or different and are independently selected from:

a bond, or one or more of phenyl, sulfur, oxygen, sulfonyl, phenylthio, phenylthiobenzenethiolyl, phenylsulfonyl, and —O-aryl, wherein the aryl is selected from the following group:

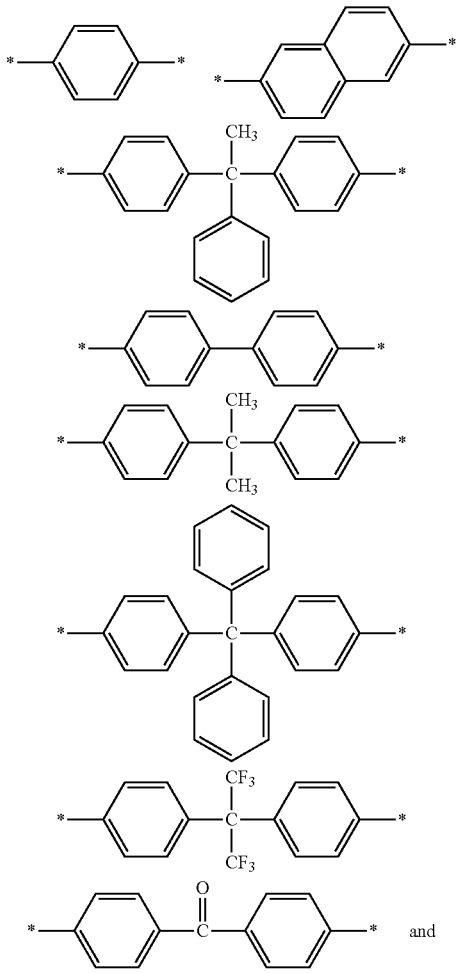

III. Poly(arylene ether) with Lithium Perfluoroethyl Sulfonate

One embodiment provides poly(arylene ether) with pendent lithium perfluoroethyl sulfonate side chains ("PAE-LiPFS"). These may have the structure shown in Formula (II):

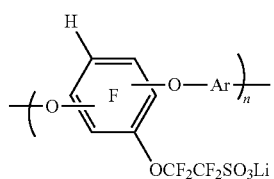

Formula (II)

where n is between 10-1000, and Ar is one or more of the following:

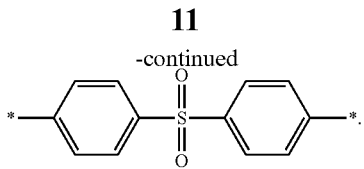

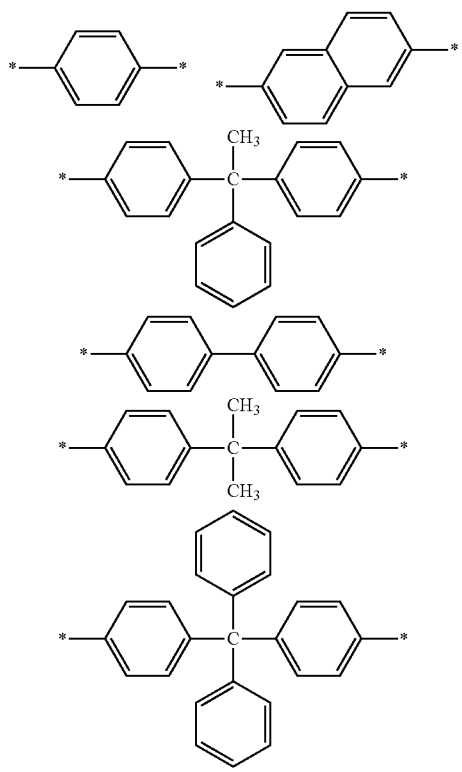

Those of skill in the art will recognize that the F, —O—, and —O—Ar are located at variable positions relative to each other and to the other substituents, as indicated by the formula.

Typically polymers of the invention are made by a condensation reaction. Two monomers each flanked by reactive functional groups react to form a linkage and a polymer chain. As those of skill in the art would appreciate, at each end of a resulting polymer chain would be one of the reactive functional groups.

These polymers may be synthesized by the general route shown below:

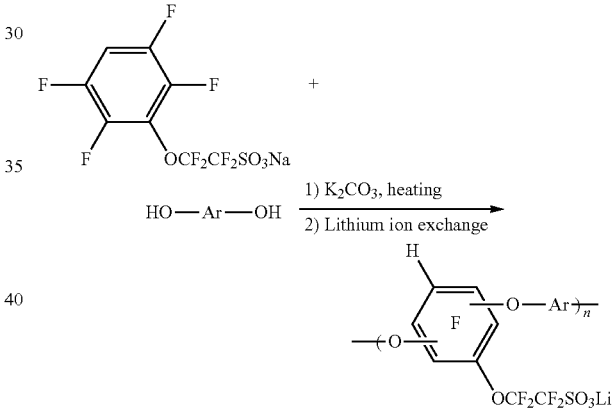

Where Ar is more than one selection from the groups listed above, then the HO—Ar—OH reagent will be replaced by two or more reagents, each with the selected group as the Ar. This may result, for example, in alternating units of the different Ar, blocks of the separate Ar, or some combination of the two.

Example 3 below, recites a synthesis of a PAE-LiPFS.

EXAMPLE 3

Synthesis of Aromatic Ionomer PAE-LiPFS

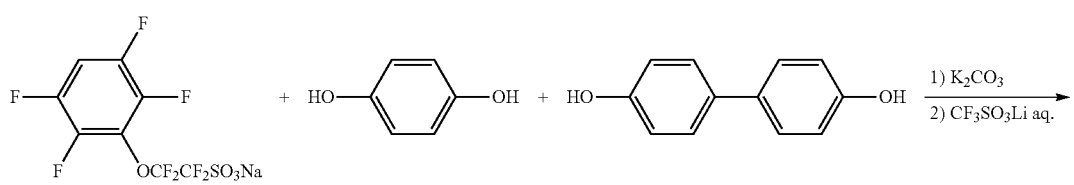

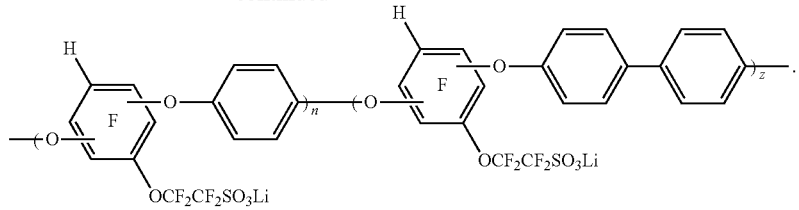

Figure 2:
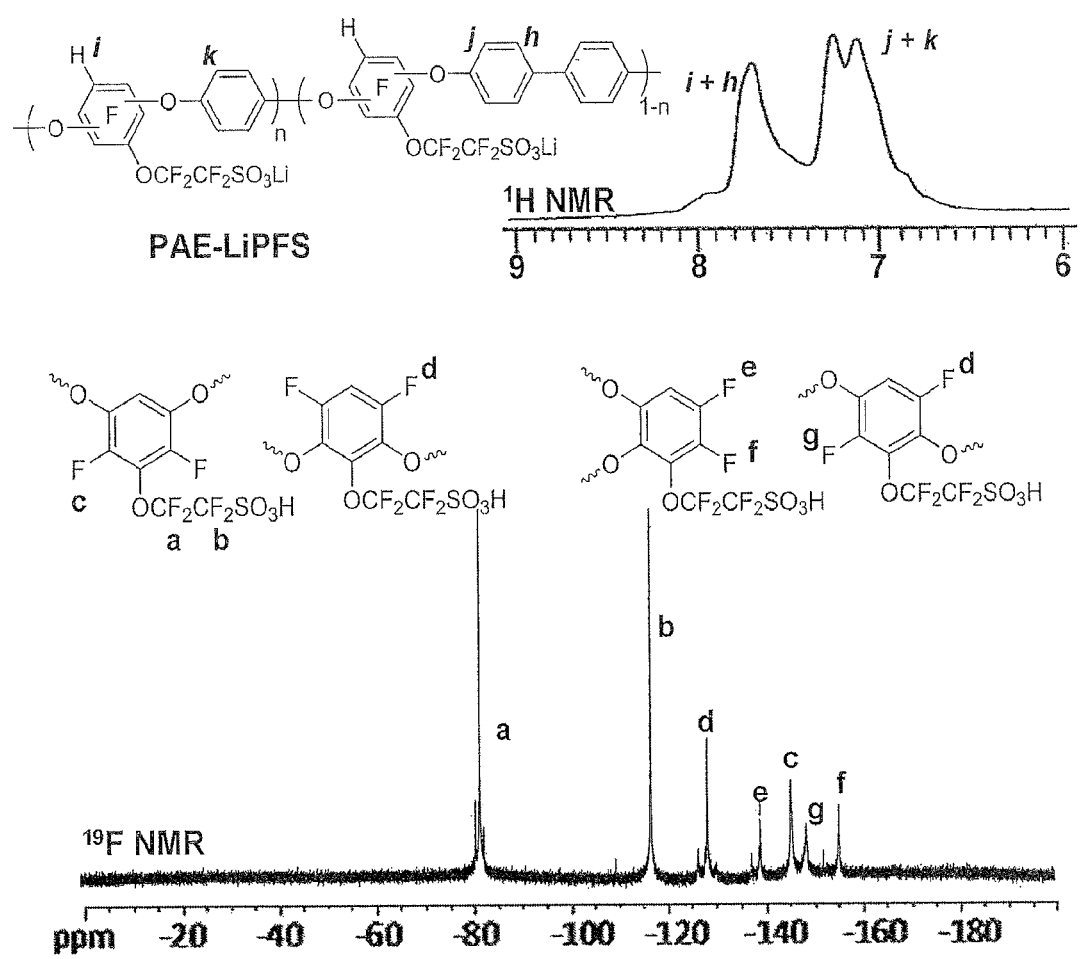
FIG. 2 shows $^1$H NMR (top) and $^{19}$F NMR (bottom) spectra of the ionomer PAE-LiPFS prepared in Example 3.

In a three-neck flask equipped with a mechanical stirrer, Dean-Stark trap, condenser, and gas inlet were added hydroquinone (7 mmol), 4,4'-biphenol (3 mmol), $K_2CO_3$ (22 mmol), anhydrous N,N-Dimethylacetamide (25 mL) and toluene (15 mL) under argon atmosphere. The mixture was heated at reflux for 2 h before the removal of toluene/water azeotrope from the Dean-Stark trap. Monomer sodium 2-(2', 3',5',6'-tetrafluorophenoxy) perfluoro-ethane sulfonate (10 mmol) was then added to the flask, and the reaction mixture was stirred at 145° C. for 16 hours. After cooling to room temperature, the reaction mixture was precipitated in water, and the precipitate was collected by filtration and washed thoroughly with water. The obtained polymer was then converted from sodium salt form into lithium salt form by immersing in 5 M lithium triflate aqueous solution at 40° C. for 24 h. After filtration and being washed thoroughly with water, the product PAE-LiPFS was dried under vacuum at 100° C. for 24 hours. $^1$H NMR and $^{19}$F NMR (FIG. 2), $d^6$-DMSO, ppm.

IV. Polyarylene Sulfides

Various embodiments of the invention also provide polyarylene sulfides and their methods of preparation and use. These may have the structure shown in Formula (II), Formula (III), or Formula (IV):

Formula (II)

Formula (III)

Formula (IV)

where n is between 10-1000, z is between 0-1000, and Ar is one or combinations of the groups consisting of:

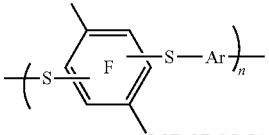

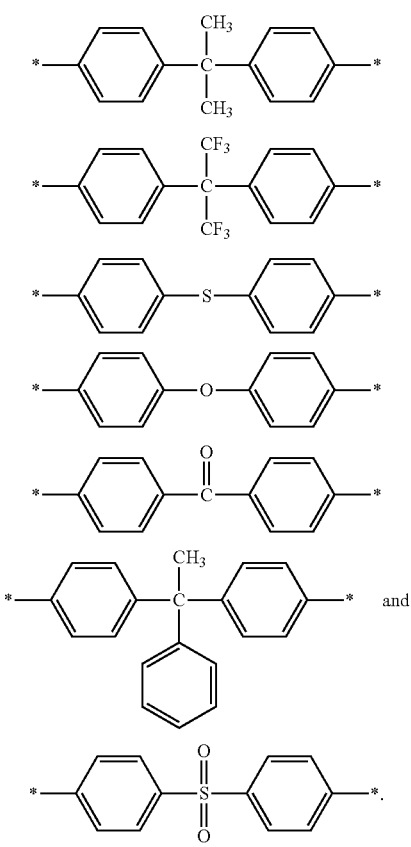

Embodiments and their preparation are shown in examples 4 and 5, below.

These polymers may be synthesized by the general route shown below:

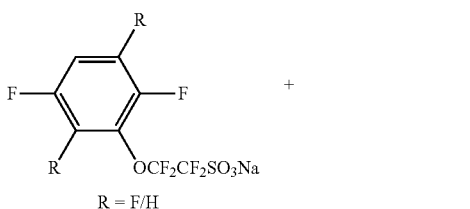

-continued

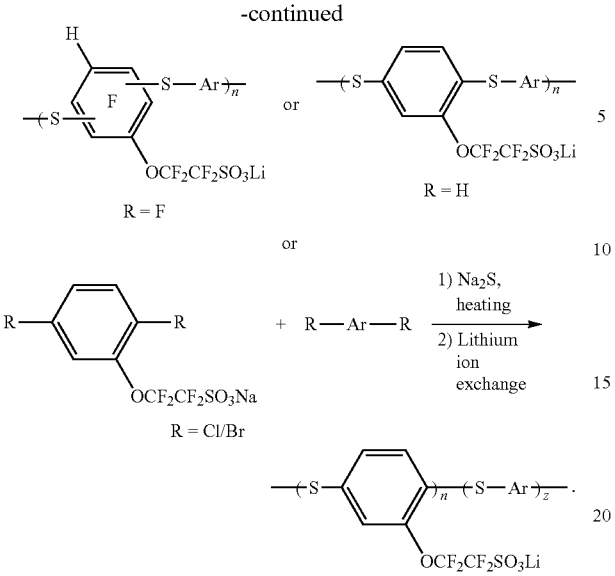

EXAMPLE 4

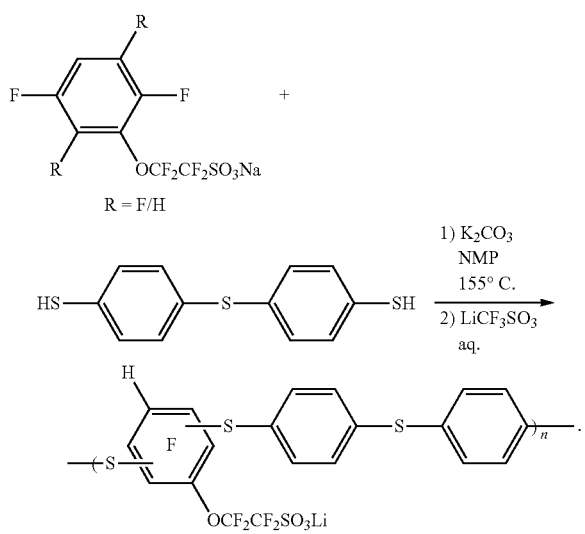

Into a three-neck flask equipped with a mechanical stirrer, Dean-Stark trap, condenser, and gas inlet were added 4,4'-thiobisbenzenthiol (10 mmol), K$_2$CO$_3$ (24 mmol), anhydrous N-methyl pyrrolidone (25 mL), and toluene (25 mL) under Argon protection. The mixture was heated at 135° C. for 4 hours before the removal of toluene/water azeotrope from the Dean-Stark trap. Monomer sodium 2-(2',3',5',6'-tetrafluorophenoxy) perfluoro-ethane sulfonate (10 mmol) was then added to the flask, and the reaction mixture was maintained at 155° C. for 20 hours. After cooling to room temperature, the reaction mixture was precipitated into de-ionized water. Residual salts in the crude product were removed in hot water for 3 hours. The obtained polymer was then converted from sodium salt form into lithium salt form by immersing in 5 M lithium triflate aqueous solution at 40° C. for 24 h. The obtained polymer was dried at 100° C. under vacuum for 24 hours.

EXAMPLE 5

Polyarylene Sulfide

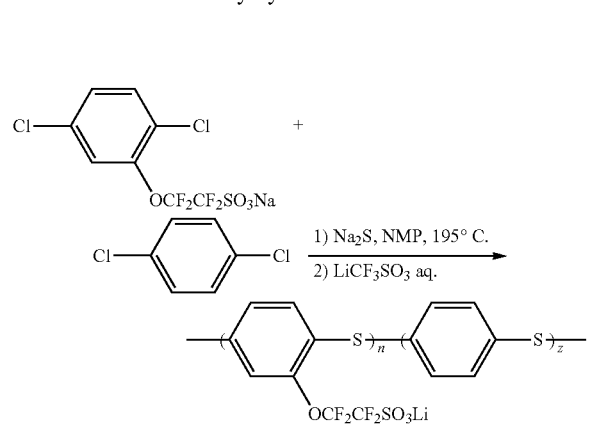

Into three-neck flask equipped with a mechanical stirrer, Dean-Stark trap fitted with a condenser and argon gas inlet were added with sodium 2-(2',5'-dichorophenoxy) perfluoro-ethane sulfonate (8 mmol), 1,4-dichlorobenzene (8 mmol), sodium sulfide nonahydrate (16 mmol), sodium acetate (18 mmol), N-methyl pyrrolidone (35 mL) and toluene (35 mL) under argon protection. The reaction mixture was heated in an oil bath at 150° C. for 4 hours before removal of toluene-water azeotropic mixture. The reaction was then allowed to proceed for 20 hours at 195° C. After cooling to room temperature, N-methyl pyrrolidone (35 mL) was added to dilute the mixture and the reaction mixture was poured into isopropanol (500 mL) to precipitate the polymer. The precipitate was separated by filtration and washed thoroughly with isopropanol. The product was further purified by re-dissolving in hot water (100 mL), precipitating in isopropanol (500 mL), washing with isopropanol, and then air-dried. In order to remove all byproduct the aqueous polymer solution was dialyzed for 10 days in de-ionized water. The obtained polymer was then converted from sodium salt form into lithium salt form by immersing in 5 M lithium triflate aqueous solution at 40° C. for 24 hours. The product was dried at 100° C. under vacuum for 24 hours.

V. Polyphenylenes

Embodiments of the invention also include polyphenylenes. These may have the structure shown in Formula (V), and Formula (VI):

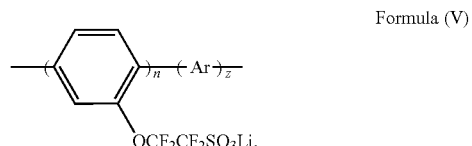

Formula (V)

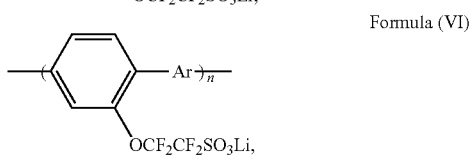

Formula (VI)

where n is between 10-1000, z is between 0-1000, and Ar is one or combinations of the groups

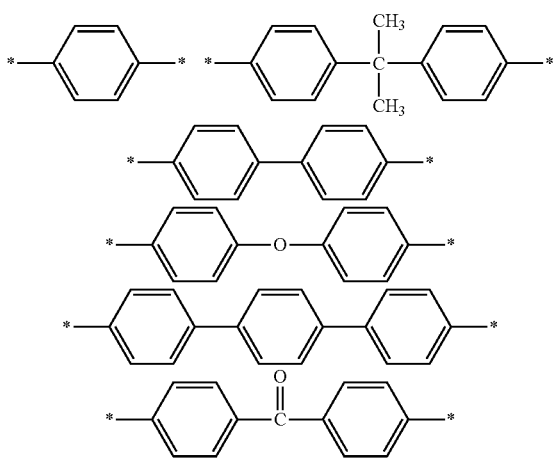

consisting of:

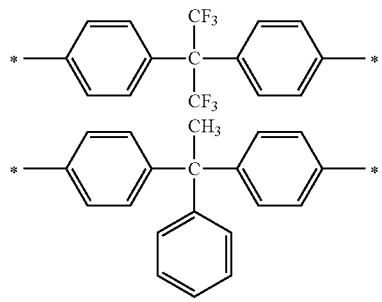

and

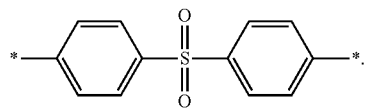

Embodiments of these are shown in the sample syntheses below, as well as in more detail in Example 6.

These polymers may be synthesized by the general route shown below:

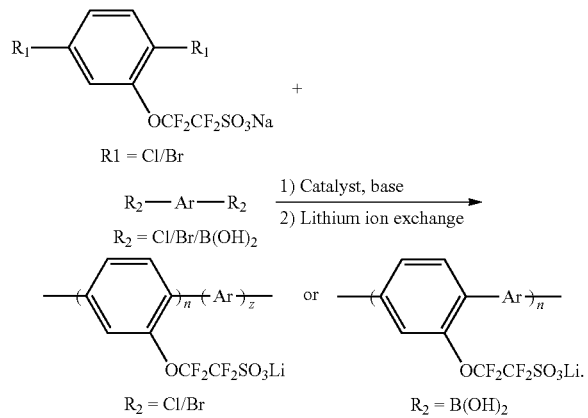

EXAMPLE 6

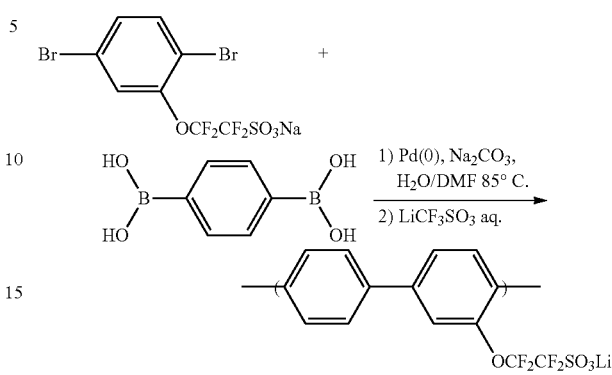

Tris[(sulfonatophenyl)phosphine]palladium(0) (90 mg) was transferred in an argon drybox to a 200-mL Schlenk flask with a magnetic stirbar. Into a separate round-bottomed flask were dissolved sodium 2-(2',5'-dichorophenoxy) perfluoro-ethane sulfonate (2.5 mmol), phenylenebis-(boronic acid) (2.5 mmol), sodium carbonate (18 mmol) distilled water (60 mL), N,N-dimethylformide (20 mL). The mixture was heated to 85° C. and stirred until the solids were completely disappeared. The solution obtained was degassed with an argon stream and transferred via cannula to the flask containing the catalyst. The mixture was then stirred at 85° C. for 10 hours under argon. The reaction mixture was evaporated afterwards by boiling until the solution volume was approximately 30 mL. A brown/tan precipitate was seen formed and collected by filtration. The solid product obtained was dissolved in hot distilled water, re-precipitated by cooling, and collected by filtration. Further purification was performed by re-dissolving the product in distilled water and conducting dialysis in water for 72 hours. Polymer was dried at 100° C. under vacuum for 24 hours.

VI. Additional Embodiments

Those of skill in the art will, with the benefit of this disclosure, recognize that a number of embodiments are encompassed within the novel teachings herein. For example, the following representative embodiments may be prepared:

A compound having the formula:

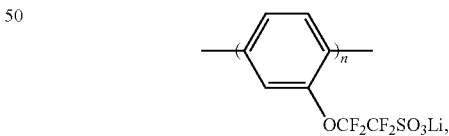

wherein n is between 10-1000.

A compound having the formula:

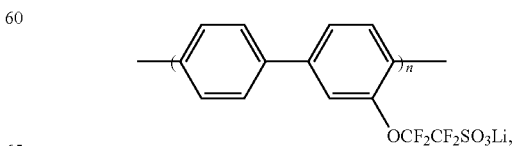

wherein n is between 10-1000.

A compound having the formula:

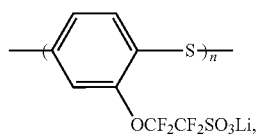

wherein n is between 10-1000.

A compound having the formula:

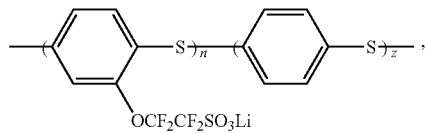

wherein n, z are between 10-1000.

A compound having the formula:

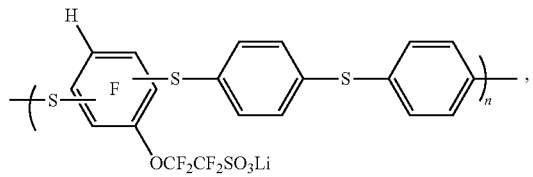

wherein n is between 10-1000.

A compound having the formula:

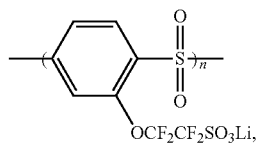

wherein n is between 10-1000.

A compound having the formula:

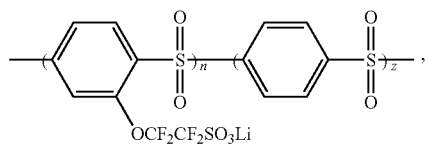

wherein n and z are between 10-1000.

A compound having the formula:

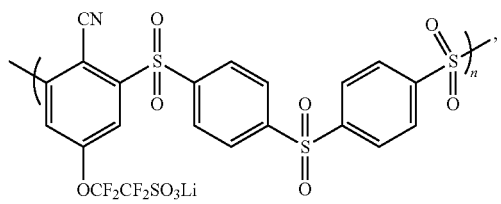

wherein n is between 10-1000.

VI. Film Formation

Typically, use of polymers of the invention in lithium-ion battery applications requires formation of a porous film. This may be accomplished, for example, by creating a solution of a polymer of an embodiment of the invention and mixing it with a water soluble oligomer. One useful oligomer is poly(ethylene glycol) dimethyl ether. The solution is then cast on a glass plate and subsequently treated with water, allowing preparation of a porous film. One example of such a film and its characterization are reported in Example 7.

EXAMPLE 7

A solution of polymer as synthesized in Example 3 (though not necessarily the actual composition created during the example that is reported), where the ratio of n to z was 0.7 to 0.3 was mixed in poly(ethylene glycol) dimethyl ether (PEG, Mw=1 000) in N, N-dimethyl formide (10 weight %) was prepared and cast onto a glass plate in an oven. The solvent was evaporated by heating the glass plate to 55° C. for 2 h and 75° C. for 4 h. The solid film obtained was then immersed in de-ionized water at 50° C. for 12 h to extract PEG. After being washed with de-ionized water thoroughly, the resulting porous polymer film was dried in vacuum oven for 24 h.

VII. Cell Fabrication

Embodiments of the invention include fabrication of electrochemical cells for lithium-ion batteries. Typically they are fabricated using carbon, LiFePO4, and a polymer of the invention. Additional materials may be included.

In one test the composite positive electrodes were fabricated by casting a slurry of LiFePO$_4$ (LFP, provided by Süd-Chemie), Super P (a carbon additive to enhance electrode conductivity), and PAE-LiPFS ionomer (as a binder) mixture dispersed in N-methyl pyrrolidinone on an etched Al foil. Several compositions were tested and it was found that the electrode which had a 18:2:5 weight ratio of LFP/Super P/ionomer showed the best charge-discharge performance, e.g. the highest specific capacity and the lowest over-potential. The electrode plate with this composition was dried overnight in air at room temperature, cut into circular disks (12 mm in diameter) and then dried overnight in a vacuum oven at 120° C. Before the cell was assembled, the membrane disks were immersed in a solution of EC/PC/DEC (1:1:1, v/v/v) for 6 h in an argon-filled glove box. The excess of solvents on the surface of the membrane disks was washed off, and CR2032-type coin cells were assembled in the glove box using lithium counter electrodes, carbonate-soaked polymer membranes, and the LFP/PAE-LiPFS composite electrodes. The galvanostatic charge-discharge and self-discharge tests of coin-type cells (CR2032) were conducted on a WBC-3000 battery cycler (Xeno Co.). The cut-off voltage limit was 2.5 ~3.9 V at room temperature.

VII. Discussion of an Embodiment

In one embodiment a polymer has the following formula, referred to generally in this section as PAE-LiPFS, but specifically known as fluorinated poly(arylene ether) lithium ethyl sulfonate:

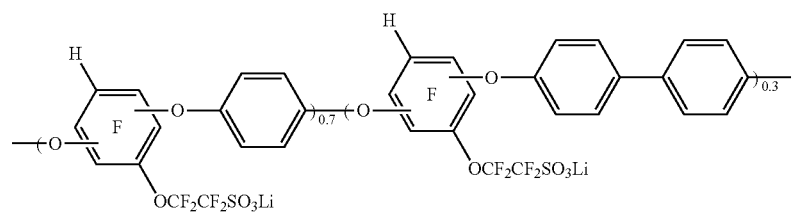

This is, of course, not the only possible embodiment, and many others are set forth below. However, the various advantages of this embodiment will now be discussed as typical of various embodiments of the invention.

The above embodiment PAE-LiPFS ionomer has been prepared via the condensation of sodium 2-(2',3',5',6'-tetrafluorophenoxy) perfluoro-ethane sulfonate (TFP) with hydroquinone and 4,4'-biphenol followed by ion-exchange with lithium salt. Strong acidic perfluorosulfonated groups were introduced to promote dissociation of the lithium cation for high conductivities. The degree of nucleophilic substitution of fluoride groups in TFP by phenolates can be readily controlled by adjusting the reaction temperature.

Only the first two phenyl fluorides of TFP are reactive when temperature is below 145° C., yielding a linear polymer that is soluble in polar aprotic solvents such as DMF, NMP and DMAc. The remaining fluorines show much lower reactivity and are only substituted above 160° C., which is probably attributed to the deactivation effect from the electron-donating ether oxygens. The remaining fluorines are anticipated to afford chemical and thermal stability to the polymer normally associated with fluoropolymers. The chemical structure and composition of the polymer have been confirmed by NMR and elemental analysis. Thermal analysis of PAE-LiPFS revealed a $T_g$ of 245° C. and an onset degradation temperature of 352° C.

Figure 3:
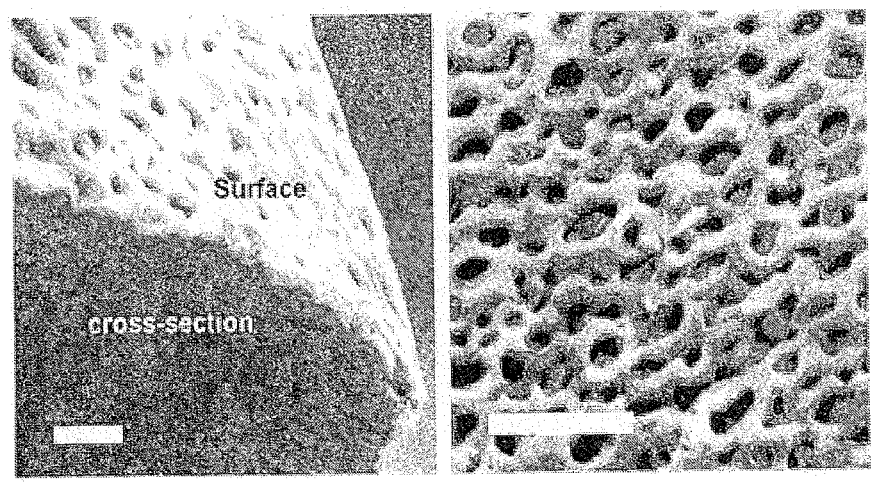
FIG. 3 shows a scanning electron micrograph of an embodiment of the invention. The bars in the figure indicate two microns in length.

Thin films with a thickness of around 45 nm were cast from a mixture of PAE-LiPFS and poly(ethylene glycol) dimethyl ether (PEG) (30 wt %) in DMF. Subsequent extraction of PEG from the films by water gave rise to a microporous film. As evidenced by scanning electron microscopic (SEM) micrographs shown in FIG. 3, interconnected hollow channels with a width range of 0.3-0.6 μm are uniformly distributed in the membrane. The porosity was estimated to be 47 wt % on basis of the film density.

Since the polymer has a hydrophobic fluorinated aromatic backbone, the inner surface of the channels is presumably rich in lithium perfluoroethyl sulfonate groups owing to their great affinity for PEG and water during the formation of pores. Accordingly, these channels are highly ionic and capable of rapidly absorbing and retaining a large fraction of water and polar organic solvents. For instance, the porous film can absorb >90 wt % water in 10 s or >85 wt % the mixture of dimethyl carbonate and ethylene carbonate (DMC+EC, 1:1 v/v) in 15 s.

Remarkably, even with considerable absorption of solvents, PAE-LiPFS membrane is still able to maintain excellent mechanical properties with free-standing, flexible and ductile film quality. The mechanical evaluation of this film reveals a Young's modulus of 310 MPa and a tensile strength of 11.7 MPa. These values signify a drastic improvement in comparison with traditional polymer electrolytes, e.g. a poly(vinylidene fluoride) (PVDF) film with a similar porosity (~48%) saturated with DEC+EC+PC has a Young's modulus of 12.2 MPa and a tensile strength of 3.9 MPa.

Although not wishing to be bound by theory, it may be that the outstanding mechanical properties of PAE-LiPFS film appear to be a direct result of a rigid aromatic polymer backbone, which enables it to function as a both separator and conductor between electrodes under pressure during the cell assembly and operation process. This is in stark contrast to conventional polymer gel electrolytes, in which the absorbance of solvents generally leads to the loss of solid state configuration and decrease of the compatibility with the lithium electrode.

Figure 4A:
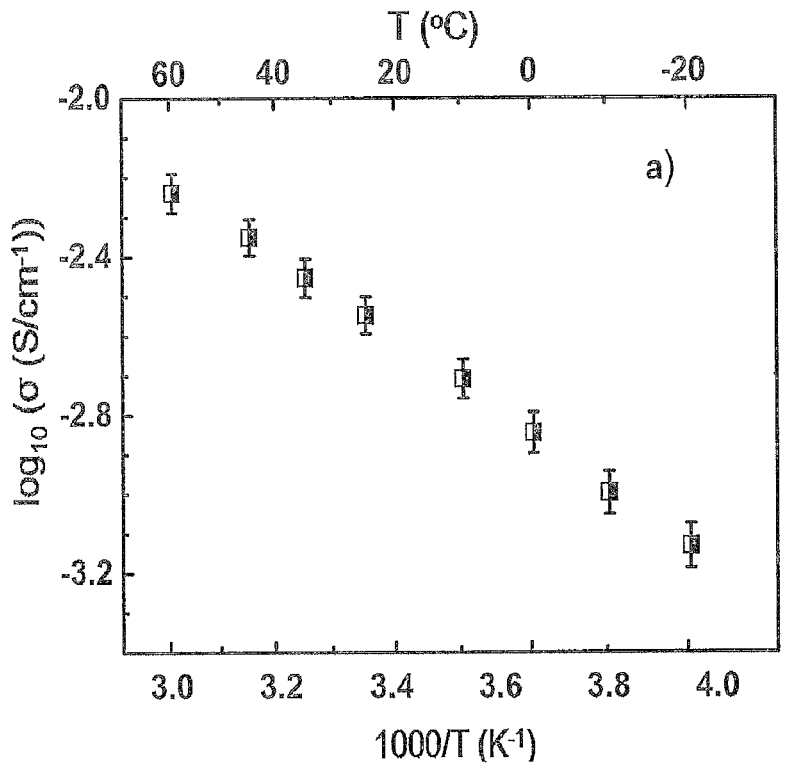
FIG. 4(top) shows Arrhenius plot of the ionic conductivity of a PAE-LiPFS/DEC+EC+PC film (1:1:1 by volume, 92 wt %).

The single-ion conducting feature of PAE-LiPFS has been confirmed by the $t_{Li+}$ measurement using the method proposed by Vincent and Bruce. A $t_{Li+}$ value of above 0.98 was obtained in hybrid PAE-LiPFS film saturated with carbonate solvents. As shown in FIG. 4a, very high Li$^+$ conductivities have been obtained in the PAE-LiPFS film soaked with DEC+EC+PC (1:1:1 by volume, 92 wt %) in a temperature range of −20-60° C. For example, the hybrid film displays a room-temperature conductivity of $3.1\times10^{-3}$ S cm$^{-1}$, which is, to our knowledge, the highest conductivity value ever achieved for single-ion conductors. Notably, the film retains sufficiently high conductivities at low temperatures, e.g. $7.4\times10^{-4}$ S cm$^{-1}$ at −20° C., implying its potential for wide-temperature-range operation.

Figure 4B:
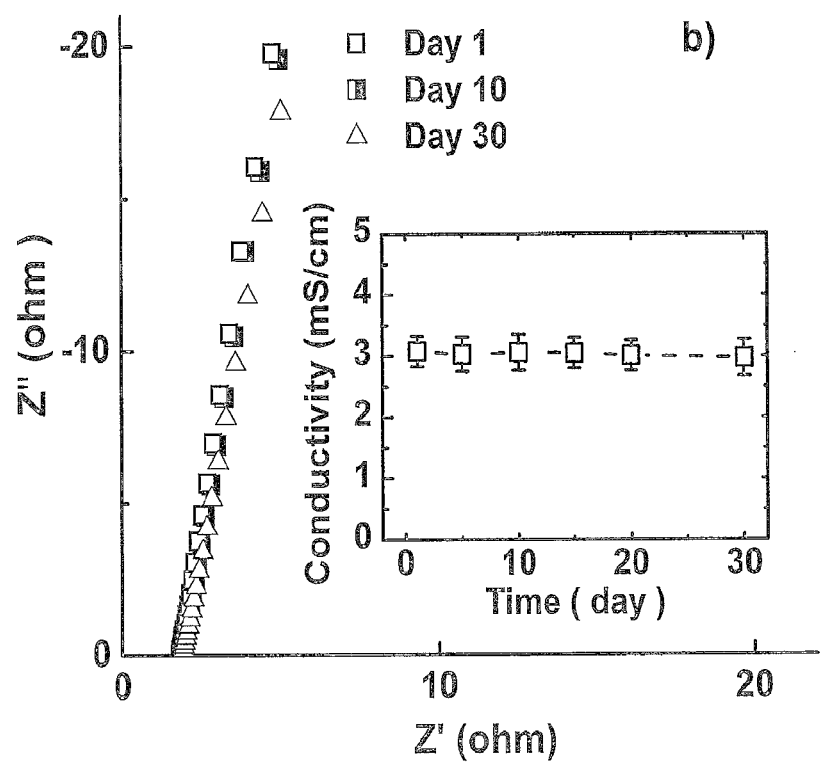

The overall temperature dependence of the conductivity exhibits an apparent Arrhenius behavior, i.e. a linear plot of log σ versus 1/T, and fitting the Arrhenius equation to the conductivity data gives an activation energy value of 17.9 kJ mol$^{-1}$. This indicates that the lithium ion transports via a hopping mechanism decoupled from the polymer segmental motion and ionic conduction occurs mainly through the entrapped solvents in the porous structure. The film impedance and conductivity of the carbonate saturated PAE-LiPFS film have been monitored for 30 days at 25° C. As shown in FIG. 4(B), negligible changes with time have been observed, indicative of great stability of the solvent-soaked film and the Li-ion conductance.

Figure 5A:
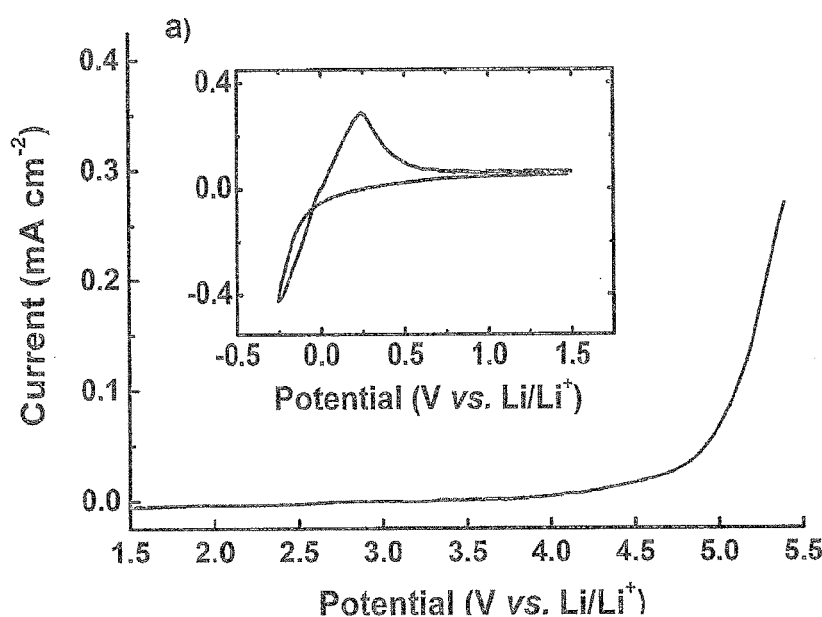
FIG. 5(top) shows a linear sweep (1.5 to 5.5 V) and cyclic voltammograms (1.5 to −0.25 V, then back to 1.5 V, in the inset) of the PAE-LiPFS/DEC+EC+PC film sealed in a cell using stainless steel as working electrode and lithium metal as counter/reference electrode (scan rate, 10 mV s$^{-1}$).
Figure 5B:
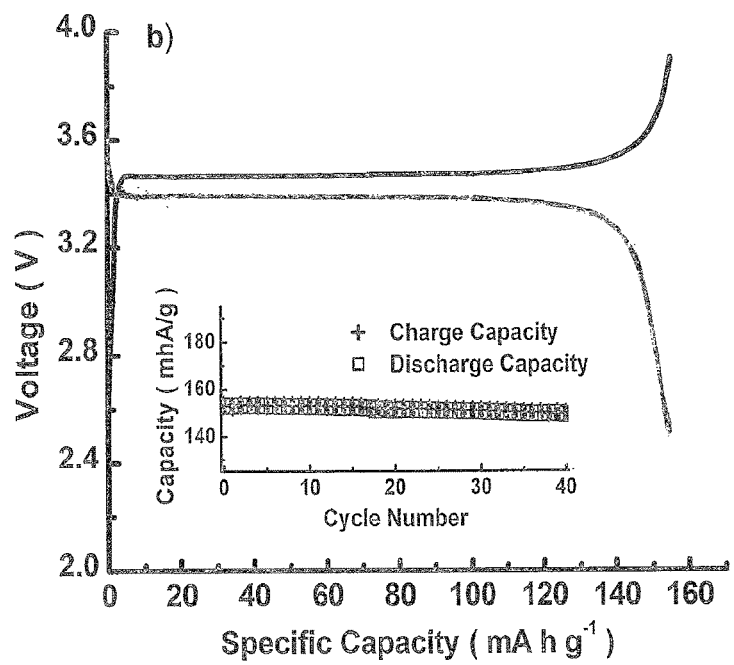

The electrochemical behavior of the PAE-LiPFS/DEC+EC+PC film was investigated by voltammetric measurements on a cell consisting of the film sandwiched between a stainless steel working electrode and a lithium metal counter/reference electrode. As shown in FIG. 5(top), the linear sweep voltammogram (1.5 to 5.5 V) indicates the film is electrochemically stable up to 4.7 V where the onset current flow states the electrochemical oxidation of the electrolyte film. In the cyclic voltammogram (the inset of FIG. 5(top)) with a potential range of −0.25 to 1.5 V, a reversible plating/stripping of lithium on the working electrode is manifest. In the catholic scan, the deposition of lithium starts at −0.05 V, and in the anodic scan, a maximum peak current at 0.25 V related to the lithium stripping is developed. These results indicate that the PAE-LiPFS/DEC+EC+PC hybrid film possesses sufficient electrochemical stability against electrode materials and lithium is capable of dissolution into and deposition from PAE-LiPFS.

The performance of the carbonate-swollen membrane, PAE-LiPFS/DEC+EC+PC, was examined in a prototype a prototype LiFePO4/membrane/Li cell. FIG. 5(bottom) presents the first galvanostatic charge-discharge voltage profile of the cell running at ambient temperature. The cell delivers a discharge capacity of 153 mA h g$^{-1}$ which amounts to 90% of the theoretical value (170 mA h g$^{-1}$). Additionally, as shown in the inset of FIG. 5(bottom), a coulombic efficiency of about 100% is maintained after 40 cycles with an excellent cyclability, and the self-discharge curve exhibits no appreciable drop in the open-circuit voltage over 1000 h. These results demonstrate that the prepared single-ion membrane is practically applicable for use in lithium-ion batteries. $^1$H and $^{19}$F NMR spectra were recorded on a Bruker AM-300 spectrometer instrument with tetramethylsilane as internal reference. Thermo-gravimetric analysis (TGA) measurements were performed on a TA instruments model 2950 at a heating rate of 10° C./min, from 30 to 800° C. under an air flow. The thermal transition data were obtained by a TA Instruments Q100 differential scanning calorimeter (DSC) at a heating rate of 5° C./min. Intrinsic viscosity were determined by a Ubbelohde viscometer using the polymer solution in DMF/0.05M LiBr (0.3 g/dL) at 25° C.

For mechanical tensile testing, the film samples were cut into dog bone shaped specimens and then tested on an Instron universal testing machine (Model 4411) at ambient conditions. Stress-strain curves were obtained at a crosshead speed of 2.0 inch/min using the ASTM D882 standard method. Through-plan conductivity (σ) of the membranes was measured by two-probe AC impedance method. Impedance data was acquired using Solartron 1260 impedance/gain phase analyzer with an AC voltage amplitude of 10 mV over the frequency range from 1 to 1M Hz. The lithium-ion transference number of the electrolyte film was measured following the procedure proposed by Vincent and Bruce. During the measurement, the electrolyte film was mounted between two lithium metal electrodes in a sealed coin cells. Voltammetry measurements were carried out on a PAR 2273 FRA/potentiostat instrument. Linear and cyclic potential sweeps were performed on the electrolyte film that is sandwiched between a stainless steel working electrode and a lithium counter/reference electrode in a sealed cell.

IIX. Ionic Liquid-Filled Porous Electrolyte Film

Although the disclosure to this point has focused on the performance of polymers as single-ion conductors, embodiments of the invention may also be useful in the presence of an ionic liquid. Such a film is not a single-ion conductor but retains utility when placed in a lithium battery. This example describes the production of a porous electrolyte film filled with an ionic liquid. A porous polymer as prepared in Example 7 (PAE-LiPFS membrane) was soaked with ionic liquids such as 1-butyl-3-methylimidazolium thiocyanate (BMIM-SCN), 1-butyl-3-methylimidazolium tetrafluoroborate (BMIM-BF$_4$) or their mixtures with propylene carbonate (PC). The porous film can absorb 60-250 wt % liquid depending on the type of the ionic liquid and PC content in the mixtures.

Figure 6:
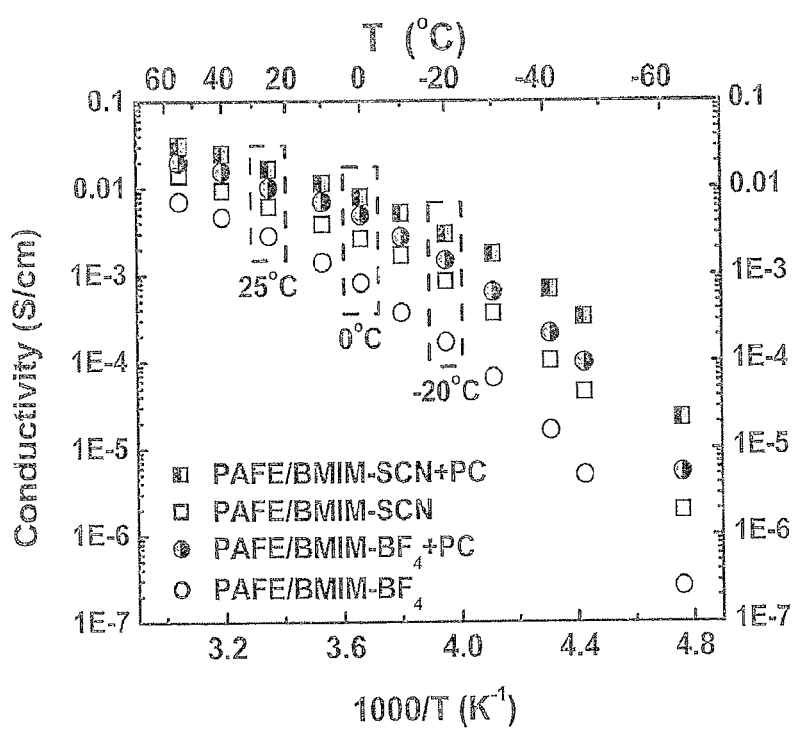
FIG. 6 shows temperature of ionic conductivity of PAFE electronic films.

FIG. 6 shows the conductivities of the PAE-LiPFS membranes containing ionic liquids and their combinations with PC over a temperature range of −63 to 56° C. We found that using a low viscous ionic liquid, 1-butyl-3-methylimidazolium thiocyanate (BMIM-SCN), in the electrolyte film led to a higher conductivity when compared with viscous 1-butyl-3-methylimidazolium tetrafluoroborate (BMIM-BF$_4$). We are aware of the adverse effect of high viscosity on ion conduction.

We also found that introducing PC solvent to the ionic liquids could further significantly improve the conductivity. For instance, at 25° C., the conductivity of the PAFE film with BMIM-SCN+PC (55:45 by volume) achieves 15.9 mS/cm, versus 6.2 mS/cm for the PAFE film with BMIM-SCN. Presumably, the highly diluted viscosity of ionic liquid by the presence of PC contributes majorly to the dramatic conductivity improvement, which agrees with reported results of the viscosity and conductivity study on the binary ionic liquid-organic solvent mixtures.

Figure 7:
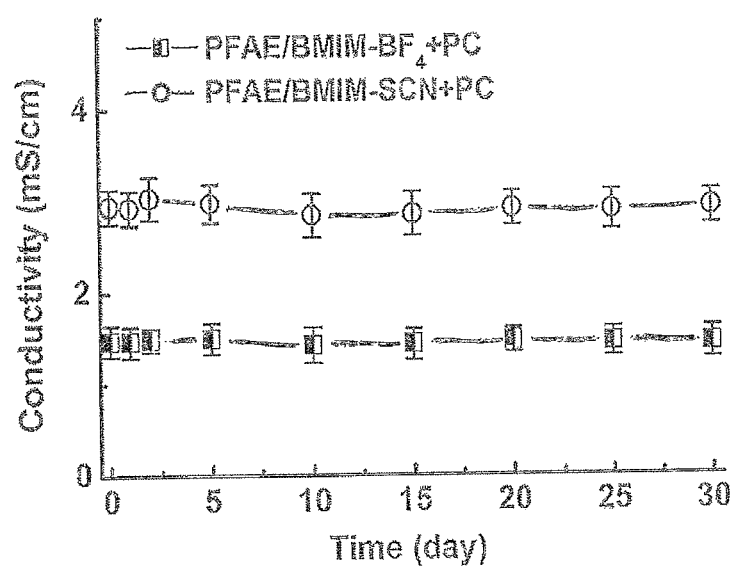
FIG. 7 shows change with time of the conductivity of PAFE electrolyte films at −20° C.

An additional contribution to the enhanced conductivity comes from the excellent lithium-ion solvation and transportation capability of carbonate solvents. Remarkably, the PAFE film with BMIM-SCN+PC (55:45 by volume) maintains outstanding ionic conductivities at low temperatures, e.g. 7.8 mS/cm at 0° C., and 2.9 mS/cm at −20° C. Even at −40° C., the conductivity of the electrolyte film still achieves 0.8 mS/cm, sufficiently high to be considered for practical use. The low temperature conductivity of the PAFE film with BMIM-BF$_4$+PC (55:45 by volume) is also notably high, which shows 4.8 mS/cm, 1.5 mS/cm at 0° C. and −20° C., respectively. It is worth noting that there are no thermal events such as crystallization and glass transitions of the ionic liquids and propylene carbonate (PC) occurring within the temperature range of interest (>−50° C.), which prevents the precipitous drop of conductivity with temperature decreasing across the thermal transition points. Furthermore, as indicated in FIG. 7, the conductivities of PAE-LiPFS membranes at low temperatures remain stable over time, indicative of their time-independent ion conduction properties.

Figure 8:
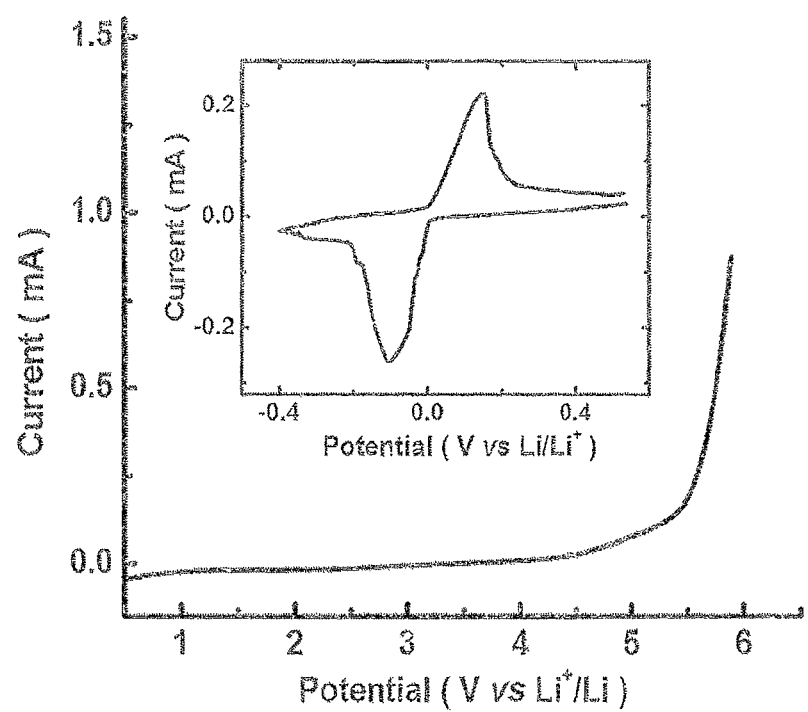
FIG. 8 shows voltammogram profiles of PAFE/BMIM-SCN+PC electrolyte film.

As shown in FIG. 8, voltammetry evaluation of the PAE-LiPFS/BMIM-SCN+PC electrolyte membranes provides information on its electrochemical stability. A linear potential sweep from 0.5 to 6 V shows an onset of a steady current increase at 4.9 V, which indicates the anodic stability limit of the electrolyte. This result demonstrates that the electrolyte film is sufficiently electrochemically stable to be used in combination with most currently available cathode materials for lithium ion batteries. Cyclic voltammogram (see the inset of FIG. 8) across a potential range of −0.4 to 0.5 V plainly shows peaks that relate to the redox processes occurring to lithium ions, including a lithium plating peak (reduction scan, from 0.5 V to −0.4 V) and a lithium stripping peak (oxidation scan, from −0.4 V to 0.5 V). These well-defined and reversible lithium plating/stripping peaks are indicative of sufficient compatibility of the PAFE/BMIM-SCN+PC electrolyte with lithium metal and capability of smooth lithium ion exchange between the electrolyte and electrode.

Although the invention has been described herein in the context of certain embodiments, those skilled in the art will recognize that other variations and modifications of the invention are possible and are within the scope and spirit of the claims.

We claim:

1. A polymer of Formula (II):

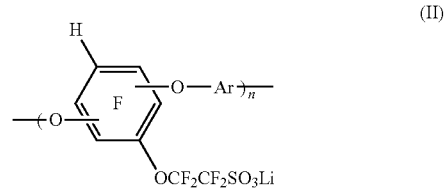

where n is between 10-1000, and wherein Ar is selected from one or more members of the group consisting of:

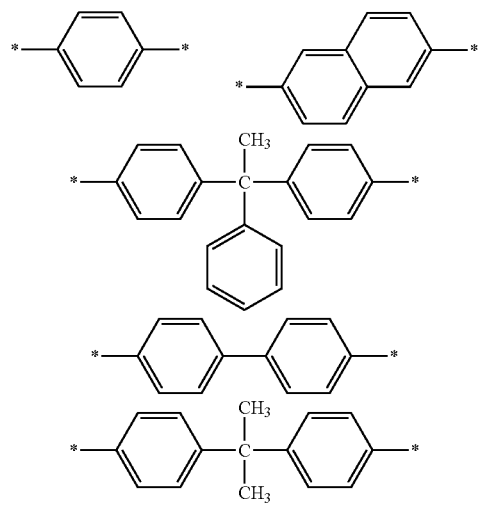

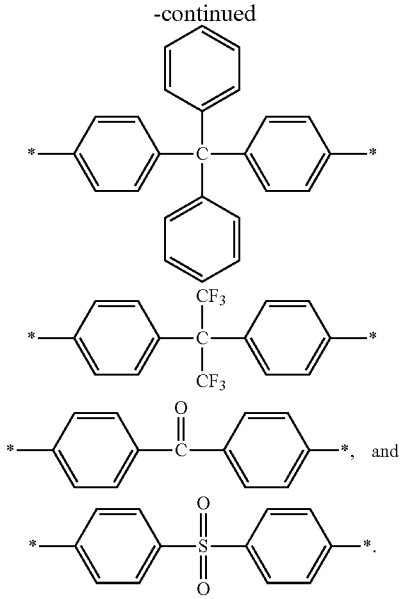

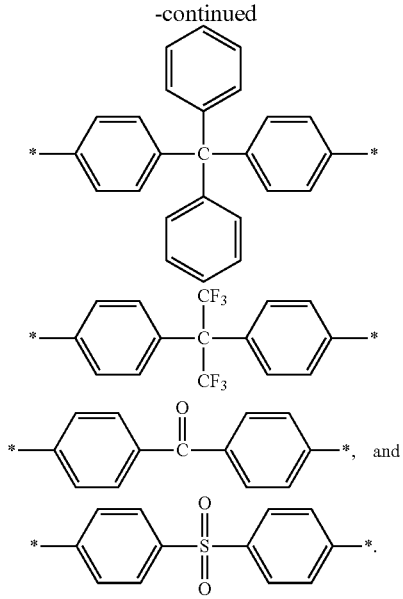

2. The polymer of claim 1, wherein said polymer is fluorinated poly(arylene ether) lithium perfluoroethyl sulfonate.

3. The polymer of claim 1, wherein Ar is

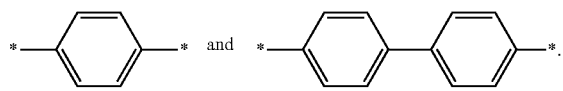

4. A porous polymer film comprising the polymer of claim 1.

5. A conductor comprising the porous polymer film of claim 1 and an ionic liquid.

6. A lithium-ion battery cell comprising a polymer of claim 1.

7. The, polymer of claim 1, wherein Ar is selected from two or more members of the group consisting of:

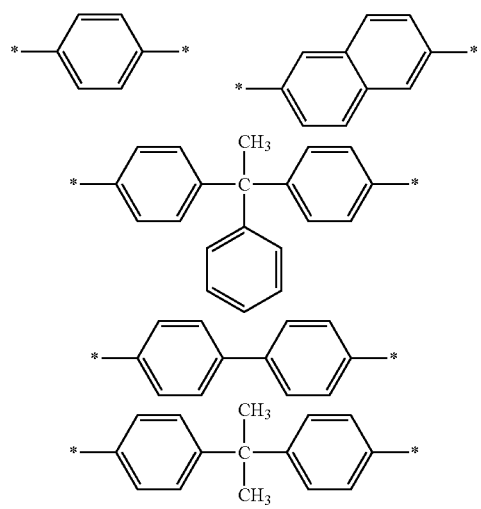

8. A porous polymer film comprising the polymer of claim 7.

9. A conductor comprising the porous polymer film of claim 7 and an ionic liquid.

10. A lithium-ion battery cell comprising a polymer of claim 7.

11. A porous polymer film comprising the polymer of claim 2.

12. A conductor comprising the porous polymer film of claim 2 and an ionic liquid.

13. A lithium-ion battery cell comprising a polymer of claim 2.

14. A porous polymer film comprising the polymer of claim 3.

15. A conductor comprising the porous polymer film of claim 3 and an ionic liquid.

16. A lithium-ion battery cell comprising a polymer of claim 3.

17. The polymer of claim 3, wherein Ar is about 70% by mole of

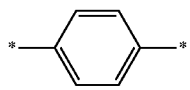 [SMILES: *c1ccc(*)cc1]

and about 30% by mole of

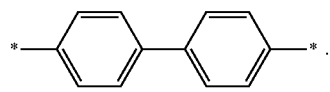 [SMILES: *c1ccc(-c2ccc(*)cc2)cc1]

18. A porous polymer film comprising the polymer of claim 17.

19. A conductor comprising the porous polymer film of claim 17 and an ionic liquid.

20. A lithium-ion battery cell comprising a polymer of claim 17.

* * * * *